(12) United States Patent
Braithwaite et al.

(10) Patent No.: US 6,299,306 B1
(45) Date of Patent: Oct. 9, 2001

(54) METHOD AND APPARATUS FOR POSITIONING SUBJECTS USING A HOLOGRAPHIC OPTICAL ELEMENT

(75) Inventors: Michael Braithwaite, Langhorne, PA (US); Jeremy Govier, Blackwood, NJ (US); Samuel P. Sadoulet, Tucson, AZ (US)

(73) Assignee: Sensar, Inc., Moorsetown, NJ (US)

( * ) Notice: Subject to any disclaimer, the term of this patent is extended or adjusted under 35 U.S.C. 154(b) by 0 days.

(21) Appl. No.: 09/540,076

(22) Filed: Mar. 31, 2000

(51) Int. Cl.[7] ............................................. A61B 3/14
(52) U.S. Cl. ............................................. 351/208
(58) Field of Search .......................... 351/212, 221, 351/204, 206, 208, 209, 246; 359/1, 19; 382/115, 117

(56) References Cited

U.S. PATENT DOCUMENTS

| 4,620,318 | 10/1986 | Hill . |
| 4,641,349 | 2/1987 | Flom et al. . |
| 4,662,730 | * 5/1987 | Outwater et al. ................ 351/212 |
| 5,194,882 | * 3/1993 | Penney ............................ 351/212 |
| 5,291,560 | 3/1994 | Daugman . |
| 5,717,512 | 2/1998 | Chmielewski, Jr. et al. . |
| 6,064,752 | * 5/2000 | Rozmus et al. ................. 382/117 |

FOREIGN PATENT DOCUMENTS

| WO 97/46978 | 12/1997 | (WO) . |
| WO 97/46979 | 12/1997 | (WO) . |
| WO 97/46980 | 12/1997 | (WO) . |

* cited by examiner

Primary Examiner—George Manuel
(74) Attorney, Agent, or Firm—Woodcock Washburn Kurtz Mackiewicz & Norris LLP

(57) ABSTRACT

A system and method of positioning an eye of a subject at a selected point in space uses a holographic optical element containing indicia. The indicia are selectively visible to a user when the user is outside a volume surrounding the selected point and direct the user toward the volume. This system can be used with a camera to take an image of the eye from which the subject can be identified.

39 Claims, 6 Drawing Sheets

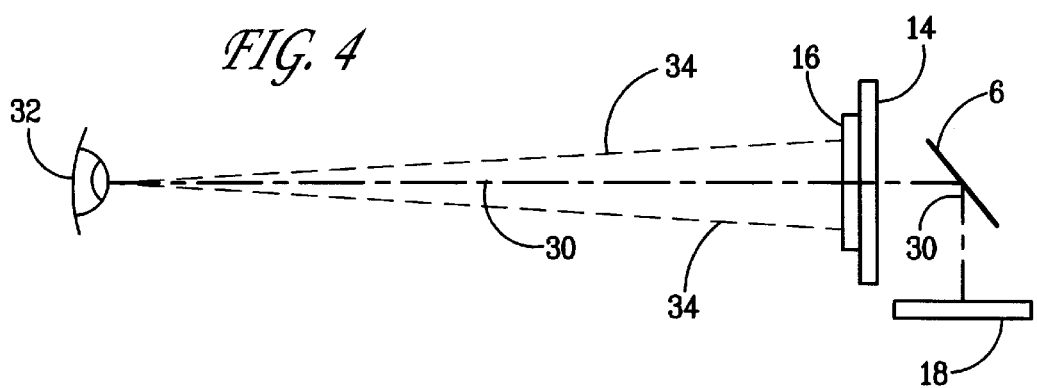
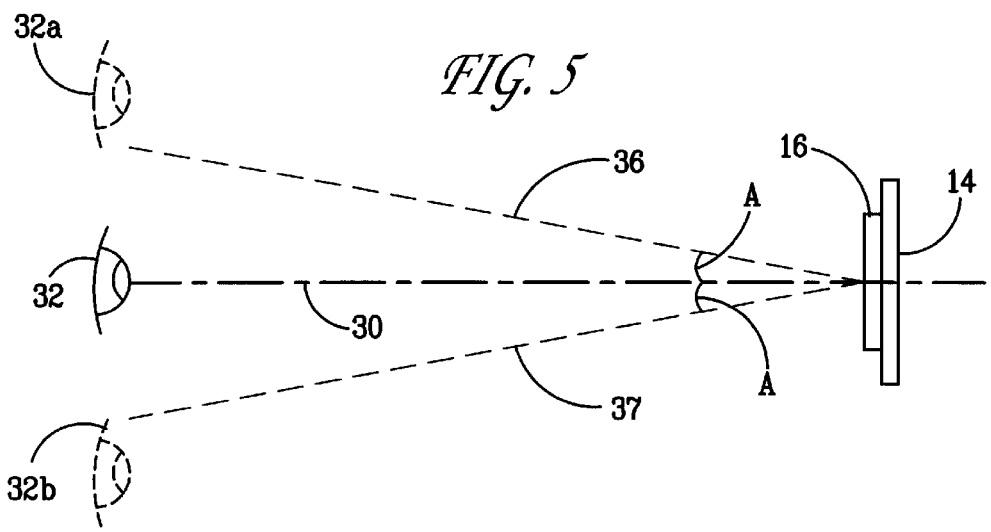
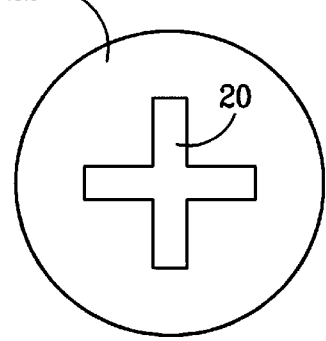 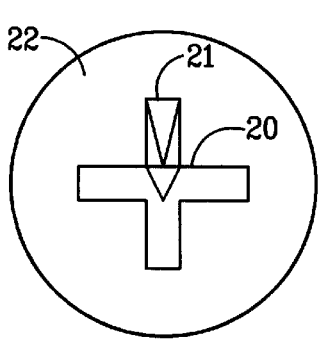 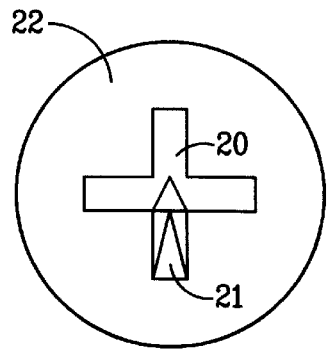

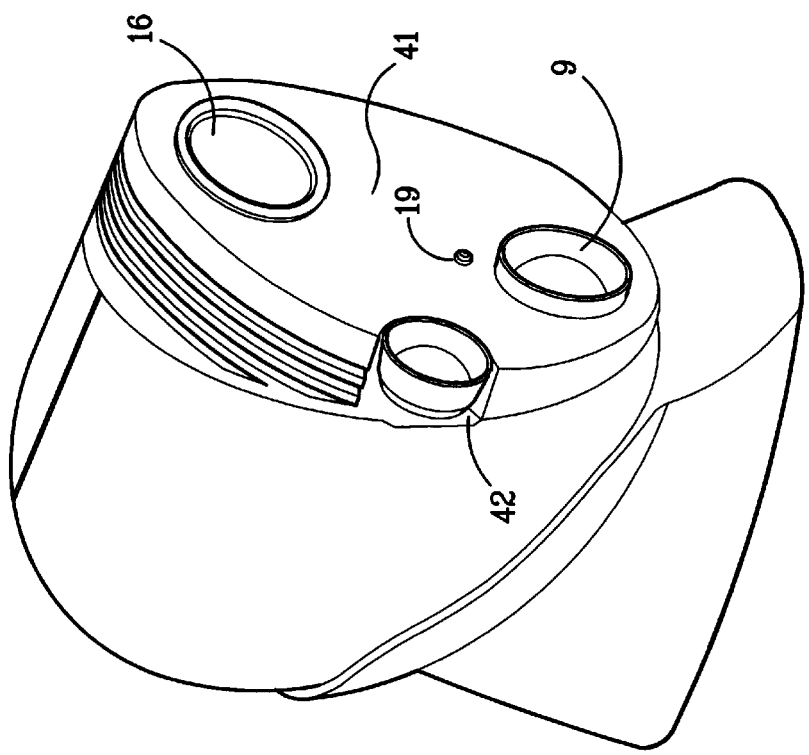
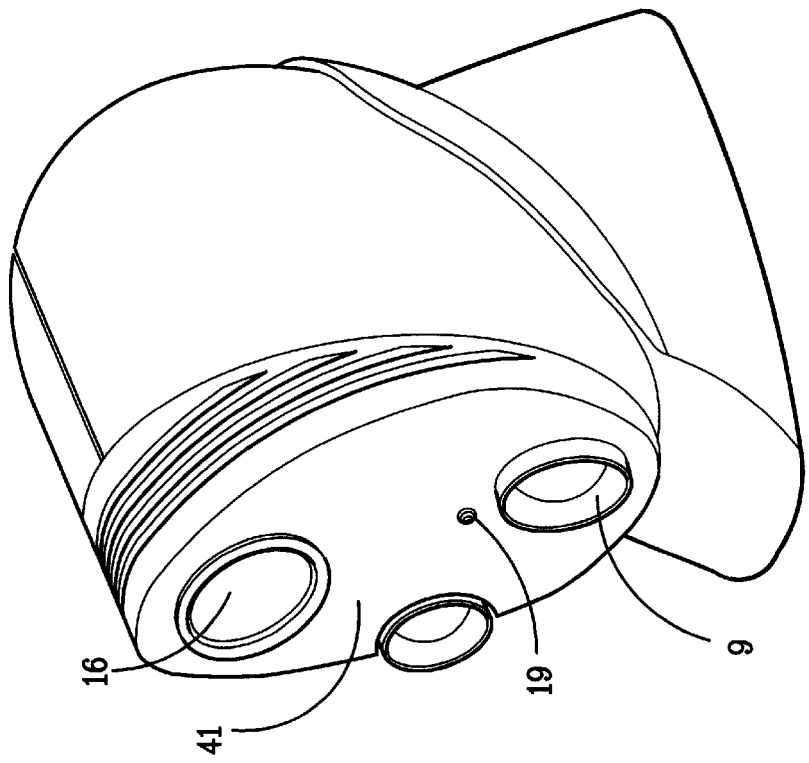

METHOD AND APPARATUS FOR POSITIONING SUBJECTS USING A HOLOGRAPHIC OPTICAL ELEMENT

FIELD OF THE INVENTION

The invention relates to devices for guiding individuals to a desired location from which they may be photographed or examined.

BACKGROUND OF THE INVENTION

There are several methods known as biometrics for recognizing or identifying an individual. Some of these methods involve imaging of the face or eye and analyzing the facial features, retinal vascular patterns of the eye or patterns in the iris of the eye. A technique for iris recognition is described in U.S. Pat. No. 4,641,349 to Flom et al. and in U.S. Pat. No. 5,291,560 to Daugman. The systems described in these references require the person being identified to hold at least one of their eyes in a fixed position with respect to an imaging camera that takes a picture of the eye.

In U.S. Pat. No. 5,717,512 there is disclosed an automated teller machine which relies upon three cameras to identify the user of an automated teller machine. The first two cameras are wide field of view cameras which find the subject's head and locate the eye position in the image. A three-dimensional position in space for the eye is calculated from the images. From that information a narrow field of view camera is directed to that position. The narrow field of view camera then takes an image of the eye from which identification can be made. Although such a system has been made to work quite well, the use of multiple cameras is expensive. Furthermore, this system occupies significantly more space than a single camera system would occupy. Thus, there is a need for a single camera system which can acquire an image of the eye useful for identification of the individual. This system should be compact, easy to use and minimally intrusive.

The popularity of the internet has opened the marketplace for electronic commerce and electronic banking. As people desire to make more expensive transactions over the internet a demand has developed for a device to assure that the person at the customer's computer is truly the person who is authorized to conduct the transaction. Iris identification has proven to be a reliable way to identify individuals. Additionally, the use of video cameras connected to personal computers has grown as cheaper digital cameras have become available. Thus, the cameras are available to provide images of computer users for iris identification. However, those cameras can only be used if the user is properly positioned for a clear, well-focused image. Hence, there is a need for a device for directing the user to the proper position from which a well-focused image of that person can be made.

Holographic optical elements having a transmission hologram are well known devices on which a viewer can see different images or portions of images according to the angle at which he views the hologram created in the holographic optical element. However, prior to the present invention the art has failed to recognize that such devices could be used to direct a user to position his eye within a selected volume of space surrounding a focal point of a camera that is used to take an image of the user's eye.

SUMMARY OF THE INVENTION

We provide a device which directs a person to a desired location at which an image of the user's eye can be taken. The device includes a holographic optical element containing a transmission hologram containing indicia that indicate to a user when the user's eye is at the desired location or direct the user to move in a direction toward the desired location. In a present preferred embodiment the indicia are a cross and radially arranged arrows. The arrows are selectively visible to a user when the user is outside a desired location and the cross is visible when the user is at a desired location. When the user sees an arrow he is outside the desired location and the arrow points in a direction that the user should move his head to reach the desired location. The user moves his head until he sees a cross and no longer sees an arrow. A single camera is positioned so that when the user sees a cross and no longer sees an arrow he is positioned along or very close to the optical axis of the camera. In a preferred embodiment there is a processor and a memory connected to the camera that evaluates the quality of images being taken by the camera. When an acceptable image has been taken a green LED may illuminate or an audible camera click will sound telling the user that an acceptable image has been found. In an alternative embodiment a range finder is connected to the camera that directs the camera to adjust its lens so that the focal point of the camera will correspond to a distance from the camera at which the user is located. The user is directed to look at the alignment device and move his head to a position where he sees a cross and no longer sees an arrow using the arrow as a guide as to the direction that he should move. Then the eye of the subject is positioned for the camera to take a well-focused image.

We may provide a light source that illuminates the subject when he is in the desired position. In a preferred embodiment we provide an infrared light source and utilize an infrared camera.

This device including the camera can fit within a small housing of only a few cubic inches. We propose to incorporate our device into a video conferencing camera or a similar camera of the type used with personal computers. When so incorporated we prefer to use a separate CCD device to take the image used for identification purposes. A CMOS device or other sensor could be used as the imager.

BRIEF DESCRIPTION OF THE FIGURES

FIG. 4 is an optical diagram for the alignment device shown in FIG. 3.

FIG. 5 is an optical diagram showing three positions of an eye along an x axis or y-axis relative to the objective lens of a camera.

FIGS. 6, 7 and 8 show the corresponding image that the eye would see on the holographic optical element when in one of the three positions shown in FIG. 5.

FIG. 9 is a perspective view of a teleconferencing camera containing our alignment device.

FIG. 10 is a second perspective view of the embodiment shown in FIG. 9.

DESCRIPTION OF THE PREFERRED EMBODIMENTS

Figure 1:
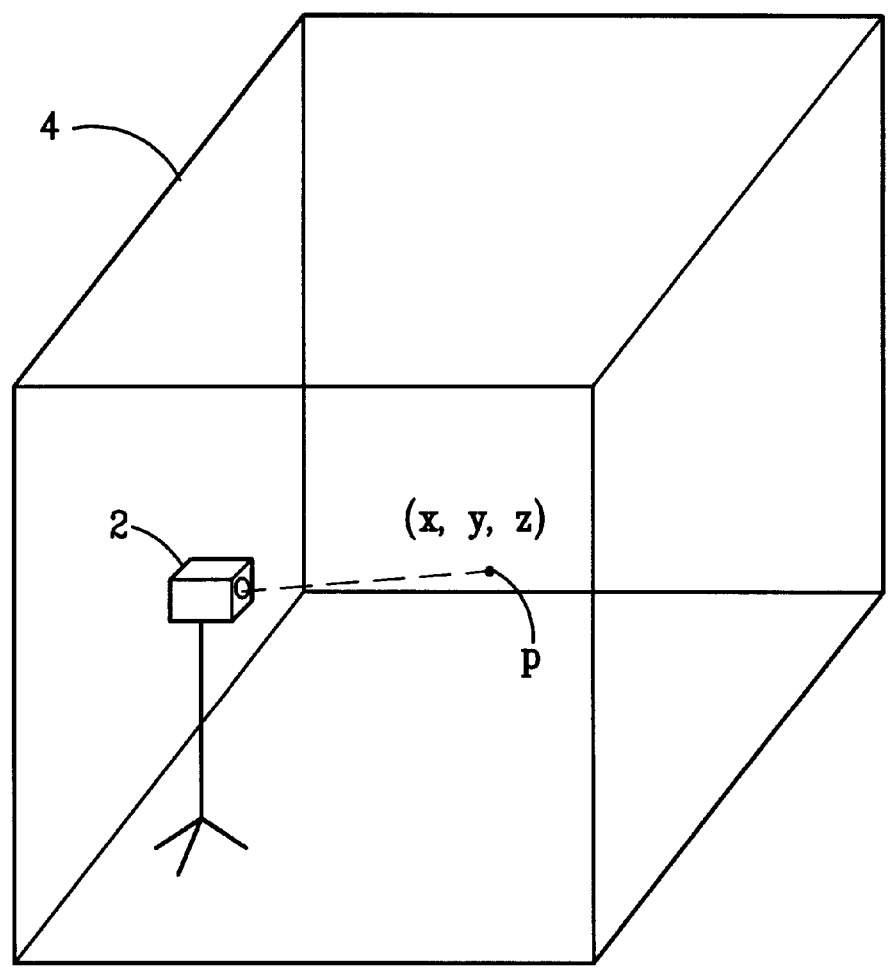
FIG. 1 is a perspective view of a camera within a room or other defined volume focused on a point (x, y, z) within the room.

The present alignment apparatus and method are intended for the situations shown in FIG. 1 where you have a camera 2 positioned within a room or other defined volume 4. The lenses of the camera are such that an object positioned at some point P in space having coordinates x, y and z will be in focus. Consequently, the camera will make a sharp, focused image of an object at that point. Since point P is determined relative to the lens of the camera, if the camera is moved the point P will also be moved to a different location within the volume. If one desires to take a clear, focused image of an object within the room 4 in FIG. 1, the object must be at or close to point P. This can be accomplished by moving the object to point P while the camera remains stationary. Alternatively, one could move the camera so that point P moves to the object. A third possibility is to move both the camera and the object. Our alignment device and method are intended for use in applications where one desires to have a clear, focused image of the eye. This image can then be used for iris identification or possibly for evaluation and treatment of the eye. Our device is intended to be attached to the camera so that one looking at the camera and particularly looking into the lens of the alignment device will know that his eye is properly positioned. When the user's eye is above, below, to the left or to the right of a desired location, the user will see an arrow or other indicia on the holographic optical element. In one embodiment the arrow or possibly two arrows will point in a direction that the user should move his head so that his eye will be at a desired location along an x direction and along a y direction. When the user does not see an arrow his head is properly positioned along the x, y axes. In another embodiment the user will only see certain indicia, such as a cross shape, when the user's eye is at a desired location.

Figure 2:
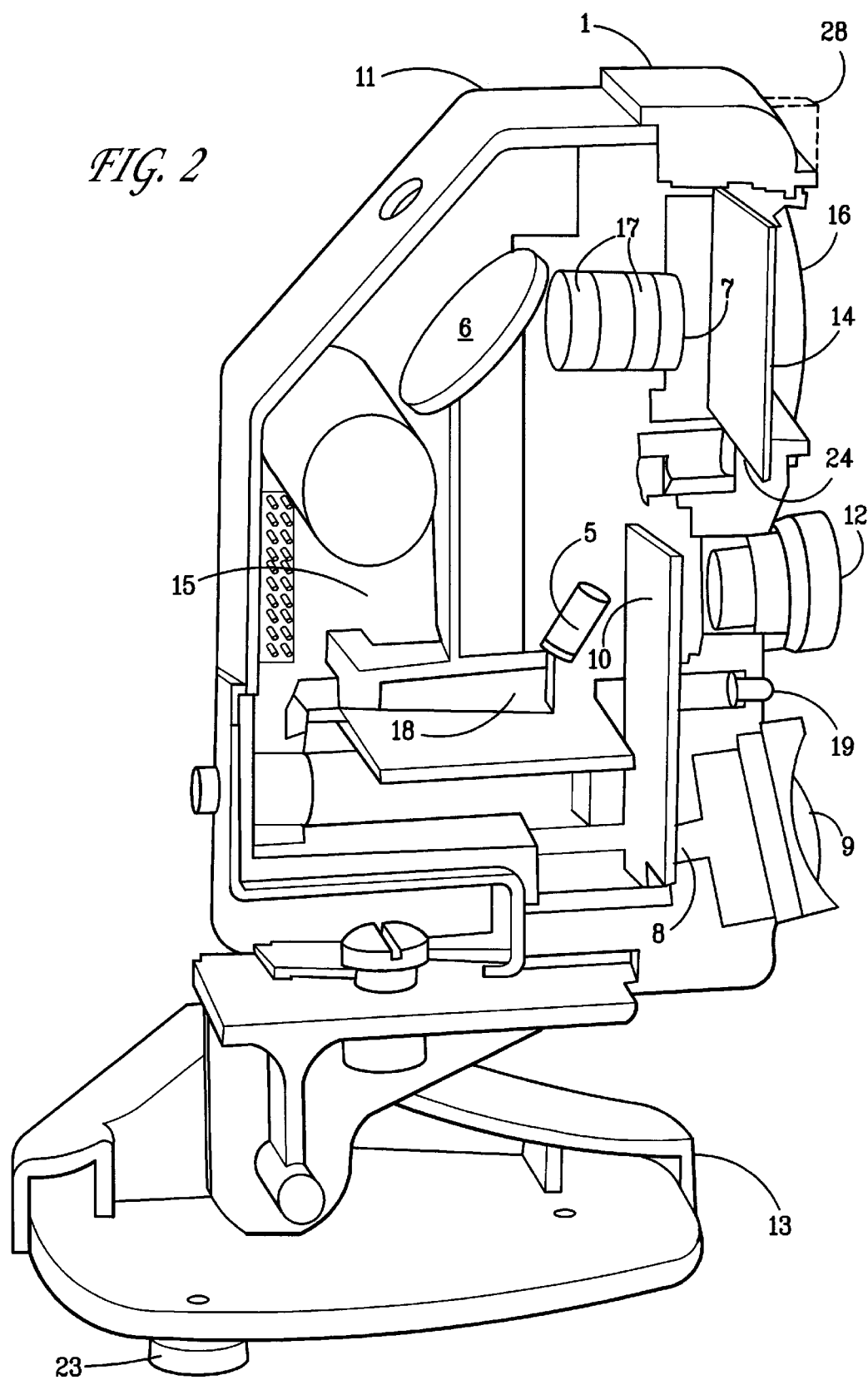
FIG. 2 is a perspective view of a present preferred camera containing the alignment device of the present invention wherein one side of the camera has been cut away.

A present preferred embodiment of an alignment and imaging device 1 shown in FIG. 2 contains a camera 18 and a holographic optical element 14 with lens 16 contained within a housing 11. We prefer to provide a detachable base 13 with rubber feet 23 which supports the housing 11. We further prefer to provide at least one illuminator that is comprised of a light emitting diode or LED 8 and a lens 9. Preferably the light emitting diode emits infrared light. The camera 18 can be a color video sensor such as a CCD sensor, CMOS device or other sensor. The camera motherboard 15 is also within the housing 11 and preferably contains a processor and memory. When the user is properly positioned the camera 18 takes an image of the user's eye which is transmitted to the processor. The memory contains a program for evaluating the quality of the image. If the image is in focus and meets other quality measures required to make a reliable iris identification of the user, the processor causes a green LED 19 to illuminate telling the user that an acceptable image has been obtained. Other indicators such as a tone generator or speaker could be used to notify the user. Indeed, in a present preferred embodiment we produce a click sound similar to that made by an old fashioned box camera to tell the user that an acceptable image has been obtained. If desired the memory may also contain a program which performs iris identification by comparing the image or a code extracted from the image to a file image or set of images of known users. Alternatively, the processor and memory unit which performs iris identification may be at a remote location. Indeed, we envision one embodiment of our device to be connected to a personal computer that would provide the processor and the memory required. That computer may transmit the image to a remote location for iris identification or contain the software to perform that function. For ease of illustration we have not shown the cables which would permit connection to a personal computer and which would provide power to the camera.

The holographic optical element provides the user instruction for positioning an eye within specific X, Y, and Z dimensions relative to the lens 16 and camera 18. As shown in FIG. 2, the holographic optical element is backlit by a blue LED 5. A light beam from that LED 5 is directed by mirror 6 through lenses 17 and infrared filter 7 onto the rear face 24 of the holographic optical element 14. The camera 18 positioned on an optical path that runs through the optically transparent portion of the holographic optical element 14. We prefer that the camera 18 be an infrared camera and that the holographic optical element 14 be transparent to infrared and opaque to visible light. When the user is positioned at the desired location by following the prompts from the holographic optical element he will be in the depth of field of camera 18. Then a well-focused image of the user's eye can be taken for use in iris identification.

Figure 3:
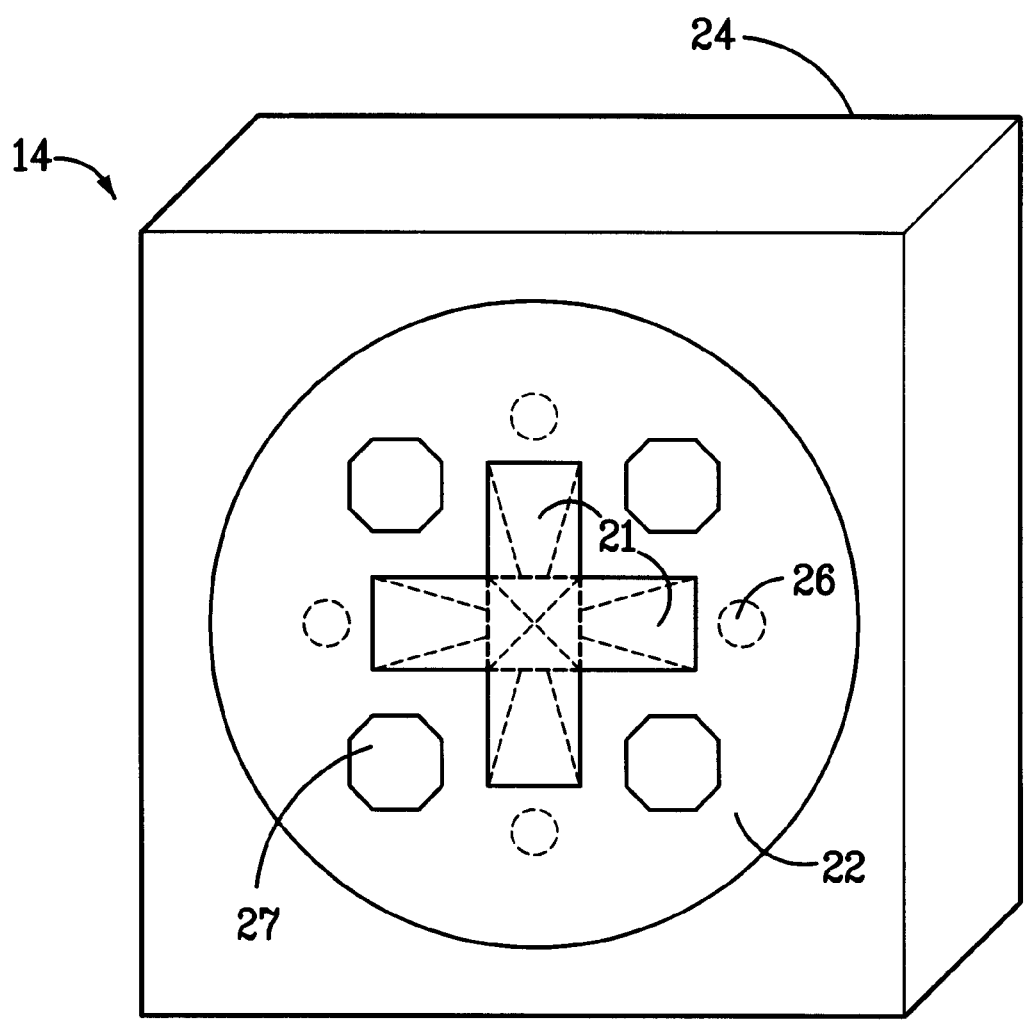
FIG. 3 is front view of a present preferred holographic optical element used in the camera shown in FIG. 2.

The holographic optical element 14 shown in FIG. 3 has a hologram consisting of a cross 20 in the center of the visible front face 22 of the optical element and four arrows 21 spaced radially 90° apart. The cross is optically transparent to the camera and can be seen by a user who is at a desired location. The arrows are positioned so that they can only be seen when the user's eye is outside the desired location. More particularly, the user sees an arrow when the observer is more than ±2.9 degrees away from the optical axis of the camera. For that reason the arrows 21 which have a triangular head and a triangular tail are shown in dotted line in FIG. 3. The holographic optical element 14 preferably is a photopolymer material within a frame. Each arrow is layered into the cross intentionally in order to minimize or eliminate the arrow being seen by one eye (e. g. left eye) while the other (the right eye) sees the cross. The cross is "burned" in the holographic optical element to be dominant when both the cross and any arrow are observed together.

Those skilled in the art will recognize that lens 16 could be an auto-focus lens that is controlled by the processor. A similar effect could be obtained by placing camera 18 on a moveable platform which allows the camera 18 to be movable along the optical path to lens 16. Another alternative is to enable both lens 16 and camera 18 to be moveable along the optical path.

If desired a second camera 10 can be provided within the housing 11 which is used for purposes other than identification of the user. For example, the camera could be a wide field of view camera with a wide filed of view lens 12 that is used for teleconferencing. The second camera may be a security camera such as the security camera in an automated teller machine into which our alignment and imaging device has been incorporated.

The use of the holographic optical element can be better understood from FIGS. 4 through 8. As shown in FIGS. 4 and 5, the camera 14 has an optical axis 30 which is reflected by mirror 6 and passes through the holographic optical element 14 and lens 16. When the user's eye is positioned on the optical axis 30, the user can see the holographic optical element 14 as indicated by sight lines 34. When the eye is on the optical axis 30, the user will see only a cross on the holographic optical element as shown in FIG. 6. When the user positions his eye sufficiently away from the optical axis 30 in a plus direction, indicated by eye 32a shown in dotted line in FIG. 5, the holographic optical element will appear as in FIG. 7. The user will see an arrow 21 pointing in a negative direction which tells the user to move his head in that direction. Should the user position his eye sufficiently far away from the optical axis 30 in negative direction, indicated by eye 32b shown in chain line in FIG. 5, the holographic optical element will appear as in FIG. 8. The user will see an arrow 21 pointing in a positive direction which tells the user to move his head in that direction. The region in which the eye may be positioned to see only the cross 20 without any arrows will be within sight lines 36 and 37 shown in FIG. 5. Those sight lines are at an angle A. In a present preferred embodiment angle A is ±2.9 degrees from the optical axis 30 of the camera 18. There will be a region further from the optical axis than are eye positions 32a and 32b where the user will not see the face of the holographic optical element. Although the drawings illustrate movement along the y-axis, a similar result would occur during movement in along the x-axis. However, in that instance the arrows would appear at the three or nine o'clock position rather than the twelve or six o'clock position. Thus, the arrows tell the user to move your head left, right, up or down.

Positioning in the Z-axis is accomplished by the user moving his head toward or away from the camera. The user is instructed to move his head to a position within a selected distance of the lens 16. As the movement occurs the camera takes images that are sent to a processor having a memory for quality checking. The processor evaluates the quality of images being taken by the camera. When an acceptable image has been taken a green LED 19 may illuminate or an audible camera click will sound telling the user that an acceptable image has been found. In an alternative embodiment a range finder 28, shown in chain line in FIG. 2, is connected to the processor which directs a camera which has an adjustable lens. The user is told to position himself in front of the camera so that he sees a cross and does not see an arrow on the holographic optical element and to hold still and await a signal. The processor directs the camera to adjust its lens so that the focal point of the camera will correspond to a distance at which the user is from the camera. Then the camera takes an image which is processed as previously described. The user is notified by a sound or LED when an acceptable image has been obtained. In a present preferred embodiment an acceptable image capture zone is eighteen to twenty inches in front of the camera. In any embodiment the processor may direct the camera to shut off after an acceptable image has been obtained.

Although we prefer to use arrows as indicia on the holographic optical element, other kinds of indicia could be used. For example, one could provide colored dots 26, shown in chain line in FIG. 3, at selected locations on the face of the holographic optical element 14. If the dot appears in one color, say green, that could indicate to the user to move his head toward that dot. Should another color such as red appear that would tell the user to move or not to move in that direction. Another option is to use geometric shapes as indicia. One such shape 27 may be an octagon, the shape used for stop signs, to indicate that the user should not move in the direction where the user sees the stop sign.

It may also be possible to provide a holographic optical element which gives the user direction as to movement along the z axis. For example, one could provide a dot pattern that appears as a single color, such as green, when viewed from a distance beyond the desired location. However, when the user is at the desired location the user will see distinct yellow and blue dots. Similarly, the holograph may appear to have one shape when viewed from beyond the desired location and a different shape when viewed from a desired location.

Figure 11:
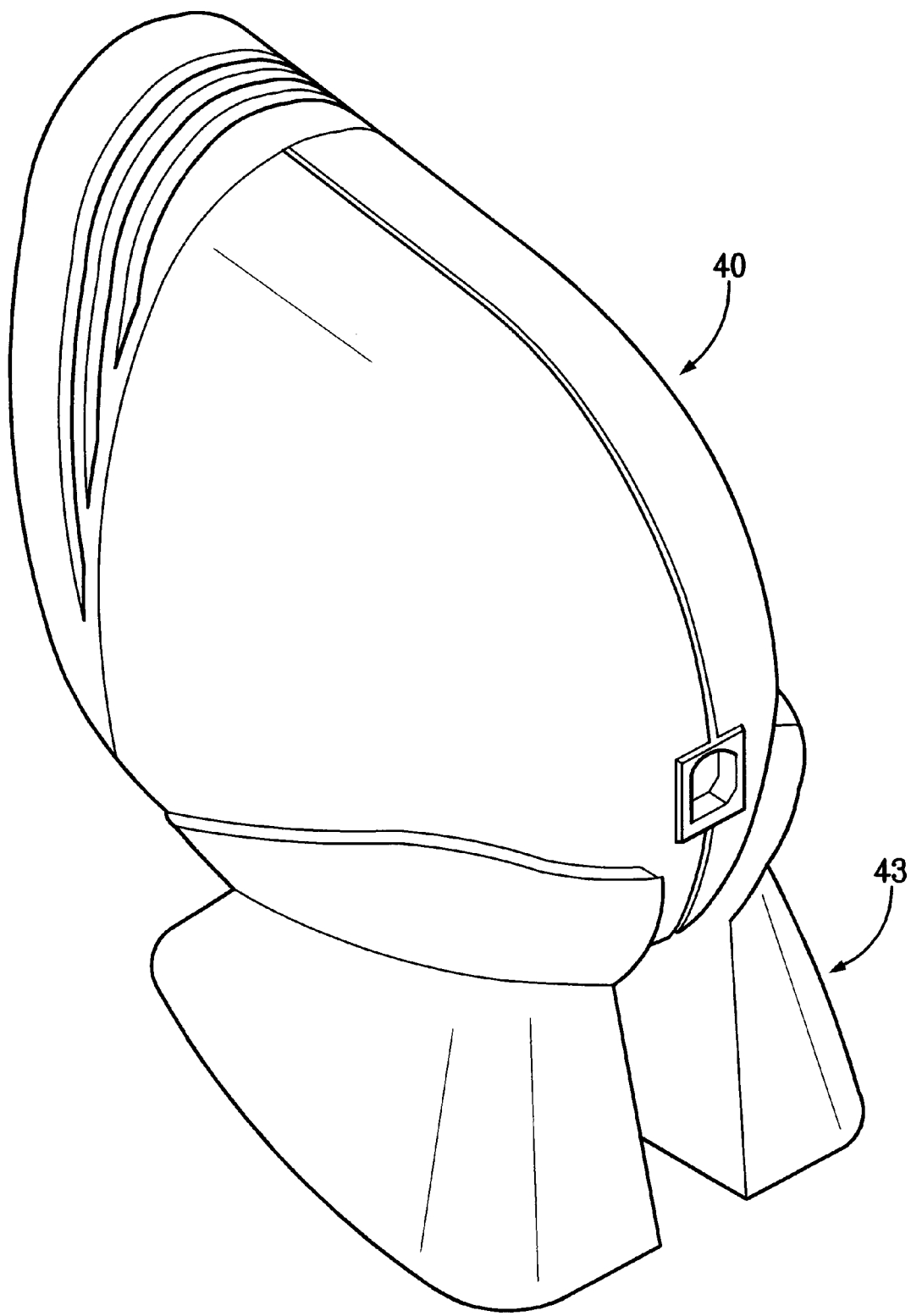
FIG. 11 is a rear view of the embodiment shown in FIGS. 9 and 10.

In another present preferred embodiment shown in FIGS. 9, 10 and 11 our alignment and imaging device is in a generally ellipsoidal housing 40 on a base 43 that also contains a teleconference camera. We prefer to place our alignment and imaging device having object lens 16 at the top portion of the housing. As in the embodiment shown in FIG. 2, we also prefer to provide light sources 8 for illuminating the subject. A wide field of view camera used for teleconferencing is behind door 41 and has a focus adjustment wheel 42. As in the first embodiment another camera (not shown) is within the housing 40 along an optical path through lens 16 and the holographic optical element is behind that lens. The structure of the alignment and imaging device in the embodiment of FIGS. 9, 10 and 11 is substantially similar to that in the embodiment shown in FIG. 2.

While we prefer to use a holographic optical element as the indicator that tells the user when he is at a desired location, other indicators that perform the same function could be used. For example, non-holographic images or symbols could be oriented to be seen when the user is at a desired location but be obscured when the user is outside the desired location. Another alternative is to provide audible signals to the user.

Although we believe our alignment system is particularly useful for positioning a subject for iris identification, our system is not limited to that use. It could be incorporated in devices for examining the eye as might be done by an ophthalmologist. It could also be used in medical applications where the individual is required to position his head at a desired location The alignment apparatus of the present invention may be mounted in other ways to maximize ease of use for the subject. For example, the device could be mounted on top of a computer monitor. The device might also be mounted on a keyboard, a door, a wall, or any other convenient location. Other configurations of the lens, camera, light source, and holographic optical element in addition to those shown in the drawings could be used. Furthermore, the holographic optical element could have more or less than four arrows. It is not even strictly necessary that the major elements of the present invention be in the same plane or that the camera be in the same housing as the light source and holographic optical element.

Although we have shown certain present preferred embodiments of our invention, it should be distinctly understood that the invention is not limited thereto, but may be variously embodied within the scope of the following claims.

We claim:

1. An alignment device for directing a user's eye to at least one selected point in space relative to the alignment device, the alignment device comprising a holographic optical element having indicia, the indicia sized and configured to indicate to a user when the user's eye is at the at least one selected point such that when the user sees an indicia that indicia will either direct the user to move in a direction toward the at least one selected point or indicate that the user's eye is at the at least one selected point.

2. The alignment device of claim 1 wherein the indicia are invisible to a user when the user's eye is at the at least one selected point and selectively visible to the user when the user is not at the at least one selected point.

3. The alignment device of claim 1 wherein the holographic optical element contains a light transmissive portion.

4. The alignment device of claim 3 wherein the holographic optical element has a front face that can be seen by the user and a rear face, also comprising a light source positioned in a optical path running from the light source to the rear face of the holographic optical element and passing through the light transmissive portion.

5. The alignment device of claim 4 wherein the light source is a light emitting diode.

6. The alignment device of claim 4 also comprising at least one mirror positioned in the optical path.

7. The alignment device of claim 1 wherein the indicia comprised of at least three radially arranged arrows pointing to a center region.

8. The alignment device of claim 1 wherein the indicia are four arrows radially arranged so that adjacent arrows are 90° apart.

9. The alignment device of claim 1 wherein the indicia are color coded regions.

10. The alignment device of claim 1 wherein the indicia are geometric designs.

11. An alignment and imaging device for imaging an eye located within a volume surrounding a selected point in space comprised of:
   a. a camera;
   b. a lens positioned to focus the camera on the selected point in space so that light reflected from an eye at the selected point in space will pass through the lens and be formed into a convergent beam which converges on the focal point of the camera; and
   c. a holographic optical element having indicia, the indicia sized and configured such that when the user sees an indicia that indicia will either direct the user to move in a direction toward the volume or indicate that the user's eye is within the volume.

12. The alignment and imaging device of claim 11 wherein the indicia are comprised of a first indicia visible to a user when the user's eye is within the volume and a second indicia visible to the user only when the user's eye is not within the volume.

13. The alignment and imaging device of claim 11 wherein the indicia are invisible to a user when the user's eye is within the volume and selectively visible to the user when the user's eye is not within the volume.

14. The alignment and imaging device of claim 13 wherein the indicia are four arrows arranged so that adjacent arrows are 90° apart.

15. The alignment and imaging device of claim 11 wherein the holographic optical element contains a light transmissive portion.

16. The alignment and imaging device of claim 15 wherein the holographic optical element has a front face that can be seen by the user and a rear face, also comprising a light source positioned in an optical path running from the light source to the rear face of the holographic optical element and passing through the light transmissive portion.

17. The alignment and imaging device of claim 16 wherein the light source is a light emitting diode.

18. The alignment and imaging device of claim 16 also comprising at least one mirror positioned in the optical path.

19. The alignment and imaging device of claim 11 wherein the camera is one of a CCD sensor and a CMOS device.

20. The alignment and imaging device of claim 11 also comprising at least one illuminator positioned to illuminate an object within the volume.

21. The alignment and imaging device of claim 20 wherein the illuminator emits infrared light and the camera is an infrared imager.

22. The alignment and imaging device of claim 11 also comprising a housing in which the camera, lens, and holographic optical element are contained.

23. The alignment and imaging device of claim 11 also comprising a second camera within the housing.

24. The alignment and imaging device of claim 23 wherein the second camera is a teleconferencing camera.

25. The alignment and imaging device of claim 11 also comprising a range finder capable of determining when the user is at a distance from the alignment and imaging device to be within the volume, the range finder being connected to the housing.

26. The alignment and imaging device of claim 25 also comprising an indicator connected to the range finder which is activated by the range finder when the user is at a distance from the alignment and imaging device to be within the volume.

27. The alignment and imaging device of claim 26 wherein the indicator is selected from the group consisting of LED's and generators of audible signals.

28. The alignment and imaging device of claim 11 also comprising a processor and memory connected to the camera which contains a program for receiving an image from the camera, evaluating whether the image is acceptable for further processing and activating an indicator which will tell the user when an acceptable image has been obtained, and an indicator connected to the processor.

29. The alignment and imaging device of claim 28 wherein the indicator is selected from the group consisting of LED's and generators of audible signals.

30. The alignment and imaging device of claim 28 wherein the lens is an auto-focus lens.

31. The alignment and imaging device of claim 28 wherein at least one of the camera and the lens are movable relative to one another.

32. An alignment and imaging device for imaging an eye located within a volume surrounding a selected point in space comprised of:
   a. a camera;
   b. a lens positioned to focus the camera on the selected point in space so that light reflected from an eye at the selected point in space will pass through the lens and be formed into a convergent beam which converges on the focal point of the camera; and
   c. at least one holographic optical element indicator positioned near the camera which tells the user either that the user is within the volume or directs the user to move in a direction toward the volume.

33. An alignment and imaging device of claim 32 wherein the indicator has indicia, the indicia sized and configured such that when the user sees an indicia that indicia will either direct the user to move in a direction toward the volume or indicate that the user's eye is within the volume.

34. A method of positioning an eye of a user within a volume surrounding a selected point in space comprising the steps of:
   a. selecting a volume surrounding a specific point in space at which an eye of the user is desired to e positioned;
   b. providing a holographic optical element indicator having indicia, the indicia sized and configured to indicate to a user when the user's eye is within the volume such that when the user sees an indicia that indicia will either direct the user to move in a direction toward the volume or indicate that the user's eye is within the volume; and
   c. instructing the subject to move his head to a position at which the indicia indicate that the user's eye is within the volume.

35. The method of claim 34 also comprising the step of taking at least one image of the eye.

36. The method of claim 34 also comprising the step of illuminating the eye.

37. The method of claim 36 wherein the eye is illuminated by an infrared light source.

38. The method of claim 34 also comprising the step of producing an audible tone after the image is taken.

39. The method of claim 34 also comprising:

a. providing processor and memory connected to the camera which contains a program for receiving an image from the camera;

b. taking an image with the camera;

c. evaluating whether the image is acceptable for further processing; and d. when an acceptable image has been obtained, activating an indicator which tells the user that an acceptable image has been obtained.

\* \* \* \* \*